United States Patent [19]

Mausner et al.

[11] 4,159,318
[45] Jun. 26, 1979

[54] OIL-FREE LIQUID MEDICATED MAKEUP

[75] Inventors: Jack J. Mausner, East Hills; Gabriel Barnett, New York; Nathan Gershaw, Commack, all of N.Y.

[73] Assignee: Helena Rubinstein, Inc., New York, N.Y.

[21] Appl. No.: 815,306

[22] Filed: Jul. 13, 1977

[51] Int. Cl.$^2$ .............. A61K 7/02; A61K 7/021; A61K 7/48
[52] U.S. Cl. ............................... 424/63; 424/69; 424/358; 424/361
[58] Field of Search ............... 424/63, 69, 358, 361

[56] References Cited

U.S. PATENT DOCUMENTS 3,639,572  2/1972  Heinrich ............................ 424/63

OTHER PUBLICATIONS

Knectel, Amer. Perf. & Cos., vol. 78, Oct. 1963, pp. 95-97.
Carlson, Amer. Perf. & Cos. vol. 86, Mar. 1971, pp. 39, 40, 42, 44.
Shevlin, Cos. & Perf., vol. 89, Jul. 1974, pp. 37, 38, 42.
Conrad, Cos. & Perf., vol. 89, Mar. 1974, pp. 33-34.
Sagarin, Cos. Sci. & Tech., Intersci Pub., NY, 1957, pp. 266-267, 329-334.
Alexander, Amer. Perf. & Cos., vol. 83, Aug. 1968, pp. 49-54.
DeNavarre, The Chem. & Mfg. of Cos., D. Van Nostrand Co., NY, 2nd Ed., vol. 2, 1962, pp. 54, 58, 59, 60-65.
Harry, Modern Cosmeticology, Chem. Pub. Co., NY, vol. 1, 1962, pp. 165-170.
Wells, Cosmetics & The Skin, Reinhold Pub. Co., NY, 1964, pp. 87-93, 125-138, 231-232, 601-602.

*Primary Examiner*—Anna P. Fagelson
*Attorney, Agent, or Firm*—Burgess, Ryan and Wayne

[57] ABSTRACT

A liquid make-up based on insoluble pigments suspended in an aqueous vehicle and completely oil-free. The composition includes emollients and pigment suspending ingredients.

4 Claims, No Drawings

OIL-FREE LIQUID MEDICATED MAKEUP

BACKGROUND OF THE INVENTION

This invention relates to cosmetic compositions, and more particularly, this invention relates to a liquid makeup having insoluble pigments suspended in an aqueous vehicle and completely oil-free.

All prior art liquid and cream makeups contain some form of oil such as mineral oil, an animal oil, a vegetable oil, or a synthetic ester such as isopropyl myristate. These oils act as an emollient to enhance dehydration of the skin and as a lubricant to impart ease of spreading. But, the presence of oil is not indicated for oily skin. Furthermore, oil may cause color-streaking or color change and, most important, it tends to clog pores and thereby interfere with normal breathing of the skin. Thus, there is a need for a makeup composition which is free of oil.

SUMMARY OF THE INVENTION

It is, therefore, a primary object of the present invention to provide a makeup composition which is oil-free.

It is a further object of the present invention to provide a makeup composition which has emollient and lubricating properties but is oil-free.

It is another object of the present invention to provide a makeup composition having no color-streaking.

Pursuant to the foregoing objects, a makeup composition is provided based on insoluble pigments suspended in an aqueous vehicle and being completely oil-free. The pigments can be any such pigments which are well-known in the art. In the preferred embodiment, the pigments are iron oxides. The aqueous vehicle contains water-soluble, non-oily, emollient and lubricating ingredients such as propylene glycol and Glucam E-20 (ethoxylated methyl glucoside). Ingredients for suspending the pigment in the medium are also included, these ingredients being Bentone LT (equal parts of hydroxyethyl cellulose and hydrous magnesium aluminum silicate) and Darvan #1 (sodium polynapthalene sulfonate).

Other ingredients such as preservatives, perfumes, and the like which are well-known in the art may be included. Furthermore, a medicated makeup is contemplated by the present invention, the composition then including well-known topical medicaments.

DESCRIPTION OF THE PREFERRED EMBODIMENT

Example 1

The composition according to a preferred embodiment of the invention is made using the following ingredients in the proportions indicated, as percentage by weight:

| PHASE A | |
|---|---|
| Deionized water | 68.33–59.08 |
| Bentone LT | 0.2–2.5% |
| Germall 115[1] | 0.35 |
| Sequestrene Na2[2] | 0.10 |
| Allantoin | 0.10 |
| Triethanolamine Regular | 0.30 |
| Glucam E-20 | 0.5–5.0% |
| Propylene Glycol USP | 20.00 |
| Methyl Paraben | 0.15 |
| Aerosol OT (70% aq soln)[3] | 0.05 |
| Cellosize WP 4400-L[4] | 0.20 |
| Darvan #1 | 0.05–2.5% |

| PHASE B | |
|---|---|
| Cosmetic Umber C33-115[5] | 9.60 |

| PHASE C | |
|---|---|
| Perfume B-6548[6] | 0.05 |
| Camphor | 0.01 |
| Menthol | 0.01 |
| | 100.00% |

[1] Imidazolidinyl urea - a preservative
[2] Ethylenediaminetetraacetic acid disodium salt
[3] Dioctyl sodium sulfosuccinate
[4] Hydroxyethyl cellulose
[5] Iron oxide pigment
[6] A facial mask fragrance mixture having a green forest blend complemented by woody, mossy, ambar and musk undertones comprised of raw materials and natural oils, the ingredients also including juniper, galbanum (a woody green note), lavendin (fresh note), rosemary, mousedechene, etc. This product is manufactured and sold by Roure Bertrand Dupont, Inc., Teaneck, New Jersey, U.S.A.

The composition is made by first charging the water to a suitable container such as a stainless mixing kettle equipped with a Lightnin' mixer. With the mixer providing fairly vigorous agitation, the Bentone LT is sprinkled in and the mixing is continued until the Bentone is completely hydrated, that is, homogeneous and lump-free. The Germall, Sequestrene, Allantoin, Triethanolamine, Aerosol, and Darvan are then added.

In a separate container equipped with a Lightnin' mixer, the propylene glycol and Glucam are charged. The Cellosize and methyl paraben are then dispersed in the propylene glycol mixture. When the propylene glycol mixture is uniform, it is added to the mixture of the other ingredients already made in the first receptacle. The pigments of Phase B are then added to the mixture and dispersed well.

When the pigments are well dispersed, the mixture is put through a colloid mill such as the Eppenbach Colloid Mill set at 0.008, into a steam jacketed stainless steel kettle equipped with a Lightnin' mixer. Heating is started as the batch is passing through the colloid mill into the kettle. This heating is done to remove air suspended in the mixture.

When the batch is completely milled, it is heated to 80° C. with stirring with a Lightnin' mixer equipped with a push-up blade. When 80° C. is reached, heating is stopped and cooling is begun. The mixture is cooled to about 50° C.

In the meantime, the camphor and menthol are dissolved in the perfume and then added to the batch which has been cooled to about 50° C. The mixture is then cooled further to about 30° C.

Example 2

The more preferred composition includes the following ingredients in the indicated percentages by weight:

| PHASE A | |
|---|---|
| Deionized water | 65.48 |
| Bentone LT | 0.40 |
| Germall 115 | 0.35 |
| Sequestrene Na2 | 0.10 |
| Allantoin | 0.10 |
| Triethanolamine Regular | 0.30 |
| Glucam E-20 | 3.00 |
| Propylene Glycol USP | 20.00 |
| Methyl Paraben | 0.15 |
| Aerosol OT (70% aq soln) | 0.05 |
| Cellosize WP 4400-L | 0.20 |
| Darvan #1 | 0.20 |

| -continued | |
|---|---|
| PHASE B | |
| Cosmetic Umber C33-115 | 9.60 |
| PHASE C | |
| Perfume B-6548 | 0.05 |
| Camphor | 0.01 |
| Menthol | 0.01 |
| | 1.00.00% |

The composition was mixed in as in Example 1. The makeup was uniform in color and non-oily. It had emollient and lubricating properties and spread evenly on the surface of the skin.

Accordingly, it will be seen that the objects set forth at the outset have been achieved. The invention has been described with reference to a present preferred embodiment which is exemplary and is not to be considered as limiting.

What is claimed:

1. A stable, oil-free liquid makeup composition consisting essentially of, in percent by weight:

| [clay] hydrous magnesium aluminum silicate | 0.1–1.25 |
|---|---|
| a bactericidal preservative | an effective amount |
| a chelating agent | an effective amount |
| allantoin | 0.10 |
| triethanolamine | 0.30 |
| ethoxylated methyl glucoside | 0.5–5.0 |
| propylene glycol | 20.00 |
| dioctyl sodium sulfosuccinate (70% aq soln) | 0.05 |
| hydroxyethylcellulose | 0.3–1.45 |
| [polymerized organic salts of alkyl aryl sulfonates] sodium polynaphthalene sulfonate | 0.05–2.5 |
| water-insoluble pigment | an effective amount |
| perfume | 0.05 |
| camphor | 0.01 |
| menthol | 0.01 |
| water | qs. 100%. |

2. A composition as claimed in claim 1, having, in percent by weight

| hydrous magnesium aluminum silicate | 0.20 |
|---|---|
| hydroxyethylcellulose | 0.40 |
| ethoxylated methyl glucoside | 3.00 |
| sodium polynaphthalene sulfonate | 0.20 |

3. A composition as claimed in claim 1, wherein said pigment is an iron oxide pigment.

4. A composition as claimed in claim 2, wherein said pigment is an iron oxide pigment.

* * * * *

UNITED STATES PATENT OFFICE
CERTIFICATE OF CORRECTION

Patent No. 4,159,318  Dated June 26, 1979

Inventor(s) Jack J. Mausner et al

It is certified that error appears in the above-identified patent and that said Letters Patent are hereby corrected as shown below:

Column 1, line 41: "polynapthalene" should be
--polynaphthalene--.

Column 2, line 15: "ambar" should be --amber--.

Signed and Sealed this

Fourth Day of December 1979

[SEAL]

Attest:

SIDNEY A. DIAMOND

Attesting Officer  Commissioner of Patents and Trademarks